United States Patent
Zemmouri et al.

(10) Patent No.: US 7,441,898 B2
(45) Date of Patent: Oct. 28, 2008

(54) METHOD AND APPARATUS FOR DETECTING NATURAL MODES OF VIBRATION OF AN EYE BY LASER INTERFEROMETRY, AND AN APPLICATION THEREOF TO MEASURING INTRAOCULAR PRESSURE

(75) Inventors: Jaouad Zemmouri, Hem (FR); Patrick Dubois, Lille (FR); Pierre-Paul Elena, Nice (FR); Jean-François Rouland, Lille (FR); Alexis Debut, Lille (FR)

(73) Assignees: Centre Hospitalier Regional Universitaire de Lille, Lille (FR); Universite des Sciences et Technologies de Lille, Villeneuve d'Ascq (FR); Universite du Droit et de la Sante de Lille, Lille (FR); Iris Pharma, La Gaude (FR)

( * ) Notice: Subject to any disclaimer, the term of this patent is extended or adjusted under 35 U.S.C. 154(b) by 1337 days.

(21) Appl. No.: 10/398,673

(22) PCT Filed: Oct. 9, 2001

(86) PCT No.: PCT/FR01/03108

§ 371 (c)(1),
(2), (4) Date: Sep. 15, 2003

(87) PCT Pub. No.: WO02/30274

PCT Pub. Date: Apr. 18, 2002

(65) Prior Publication Data

US 2004/0046937 A1    Mar. 11, 2004

(30) Foreign Application Priority Data

Oct. 10, 2000    (FR) .................................. 00 12957

(51) Int. Cl.
*A61B 3/10* (2006.01)
(52) U.S. Cl. ...................... 351/216; 351/205; 351/215; 356/454
(58) Field of Classification Search ................. 356/454, 356/480; 351/205, 209, 210, 215, 216
See application file for complete search history.

(56) References Cited

U.S. PATENT DOCUMENTS

| 3,158,674 | A | * | 11/1964 | Woodson .................. 356/4.09 |
| 5,148,807 | A |   | 9/1992  | Hsu |
| 5,638,176 | A | * | 6/1997  | Hobbs et al. ................ 356/519 |
| 5,975,699 | A | * | 11/1999 | Hellmuth .................... 351/211 |

FOREIGN PATENT DOCUMENTS

| DE | 196 47 114 A | 5/1998 |
| WO | WO 96 32054 A | 10/1996 |

* cited by examiner

*Primary Examiner*—Scott J. Sugarman
*Assistant Examiner*—James R Greece
(74) *Attorney, Agent, or Firm*—Weingarten, Schurgin, Gagnebin & Lebovici LLP

(57) ABSTRACT

The eye is positioned relative to a detection device in such a manner as to co-operate with the device to form a Fabry-Perot cavity having a main optical axis and comprising two opposite reflecting faces on the main optical axis, one of these two faces being constituted by a stationary reflecting element and the other being formed by the cornea of the eye. An incident laser beam is injected into said cavity so as to be centered on the main optical axis of the Fabry-Perot cavity, the cornea is aligned laterally and longitudinally relative to the main optical axis in such a manner as to obtain longitudinal interference between the go and the return laser beams reflected between the two reflecting faces of the cavity, and an opto-electronic detector is used to detect the intensity I of said interference as a function of time. The invention is applicable to measuring intraocular pressure.

21 Claims, 9 Drawing Sheets

METHOD AND APPARATUS FOR DETECTING NATURAL MODES OF VIBRATION OF AN EYE BY LASER INTERFEROMETRY, AND AN APPLICATION THEREOF TO MEASURING INTRAOCULAR PRESSURE

The present invention relates to detecting natural modes of vibration of an eye. A preferred but non-exclusive application of the invention lies in measuring intraocular pressure (IOP).

BACKGROUND OF THE INVENTION

In the field of ophthalmology, for example, intraocular pressure is measured to diagnose certain ophthalmological pathologies, with the main pathology being glaucoma of the eye.

Various devices are in existence at present for measuring intraocular pressure, and they can be classified in two main categories: tonometers and devices for measuring by means of laser interferometry.

Contact tonometers comprise essentially indentation tonometers, such as the Schlötz tonometer, and applanation tonometers, of which the most widespread is Goldmann's tonometer.

Indentation tonometers use a piston to deform the wall of the eye by pressing into the cornea, with IOP being measured by measuring the distance traveled by the piston. The major drawback of indentation tonometry is that account needs to be taken of the stiffness of the eye wall, and this leads-to variability of measurement from one eye to the other. That is why it can be assumed that that measuring technique is no longer in use nowadays.

Applanation tonometers use the known principle whereby the pressure which exists inside a spherical pressure chamber such as the eye has a relationship with the force which is capable of flattening a certain area of the sphere.

More particularly, amongst applanation tonometers, Goldmann's tonometer comprises a flattening cone made of plastics material containing a biprism which transforms the round image of the flattened cornea into two semi-circles which coincide when the cornea is flattened. The flattening cone is connected by a rod to a system using a calibrated spring to generate the force needed for flattening and which converts said force into millimeters of mercury (mmHg). The main drawback of that tonometer is that it is traumatizing and painful when used on the eye since a mechanical deformation force is applied to the cornea. As a result, repeated measurements on the same eye can lead to a lesion of the corneal epithelium, and in practice that method must necessarily be implemented by an ophthalmological doctor with the eye being anesthetized locally by means of anesthetic eyedrops. In spite of providing satisfactory sensitivity, there are also numerous causes of error in measurement: variability associated with tears, with accommodation, with thickness of the cornea.

A second type of applanation tonometer, also referred to as a "contactless" tonometer, uses a short puff of air to deform the cornea so as to make it concave, thus passing through a stage in which the flattened surface of the cornea presents a best angle of reflection between the light source and an optoelectronic sensor; it is this maximum which is detected and considered as the moment of measurement. The time that elapses between the beginning of the puff of air and maximum reflection on the cornea can be converted into a value for intraocular pressure. That type of tonometer likewise requires harmful mechanical deformation of the cornea.

More recently, devices have been proposed for measuring intraocular pressure by laser interferometry, with the major advantage of avoiding any application of a mechanical pressure force that is exerted on the cornea in order to deform it while making the measurement. Such devices rely on setting the eye into vibration, for example by means of a soundwave, and on using a Michelson type interferometer to detect the frequencies of natural modes of vibration of the eye. Work has shown that there is a simple relationship between the frequencies of the natural modes of vibration of the eye and intraocular pressure.

An example of that type of device is described in international patent application WO-A-93/21820. In that type of interferometer, the main incident laser beam is split by a splitter mirror (referenced 46 in the embodiment shown in FIG. 2 of WO-A-93/21820) into two secondary incident beams that are oriented at 90° to each other, one of the two secondary incident beams is reflected by the surface of the cornea of the eye, while the other secondary incident beam being reflected by a mirror (referenced 70 in the embodiment of FIG. 2 of WO-A-93/21820). The two return beams as reflected respectively by the cornea and by the mirror return to the splitter mirror where they interfere. A major drawback of that device is that in order to obtain interference, it is essential for the return beams to be accurately colinear. As a result, the cornea must be accurately in alignment relative to the splitter mirror, and it is not possible to accept the slightest lateral or longitudinal misalignment of the cornea, which makes taking a measurement very constraining in terms of eye positioning. Another result is that that device is extremely sensitive to the slightest external disturbances which might modify the alignment of the optical system very slightly, and in particular it is very sensitive to the slightest movement or mechanical vibration of the device. Another drawback of that type of device is that detecting the natural frequencies of vibration of the eye by measuring the intensity transmitted by the interferometer makes it necessary, in practice, to use a high power laser, with the risk of creating a lesion of the cornea. Finally, in international patent application WO-A-93/21820, the eye is excited in order to set it into vibration using a harmonic method by sweeping the frequency of the excitation soundwave. That harmonic excitation method presents the drawback of increasing the length of time required for measurement, and above all the soundwave may be traumatizing for the eardrum.

OBJECT AND BRIEF SUMMARY OF THE INVENTION

The invention seeks to propose a novel method of using laser interferometry to detect one or more natural modes of vibration of an eye, but which compared with the above-described methods based on using a Michelson type interferometer, presents the main advantages of being less constraining on eye positioning, of being less sensitive to external disturbances, and in particular mechanical vibration, and of making it possible to use a lower power laser.

More particularly, the above-mentioned advantages of the invention make it possible to provide a detector device of outpatient type, it being specified that the invention is nevertheless not limited to this outpatient aspect.

In the method of detection of the invention the eye is positioned relative to a detection device so as to cooperate with the device to form a Fabry-Perot cavity comprising two opposite reflecting faces on the main optical axis of the cavity, one of these two faces being constituted by a stationary reflecting element and the other being formed by the cornea of the eye; an incident laser beam is injected into said cavity, the beam being centered on the main optical axis of the Fabry-Perot cavity, the cornea being aligned laterally and longitudinally relative to the main optical axis in such a manner as to obtain longitudinal interference between the go and the return laser beams reflected between the two reflecting faces of the cavity; and an optoelectronic detector is used to detect the intensity I of said interference as a function of time.

BRIEF DESCRIPTION OF THE DRAWINGS

Other characteristics and advantages appear more clearly on reading the following description of an embodiment given by way of non-limiting example and with reference to the accompanying drawings, in which.

MORE DETAILED DESCRIPTION

Figure 1:
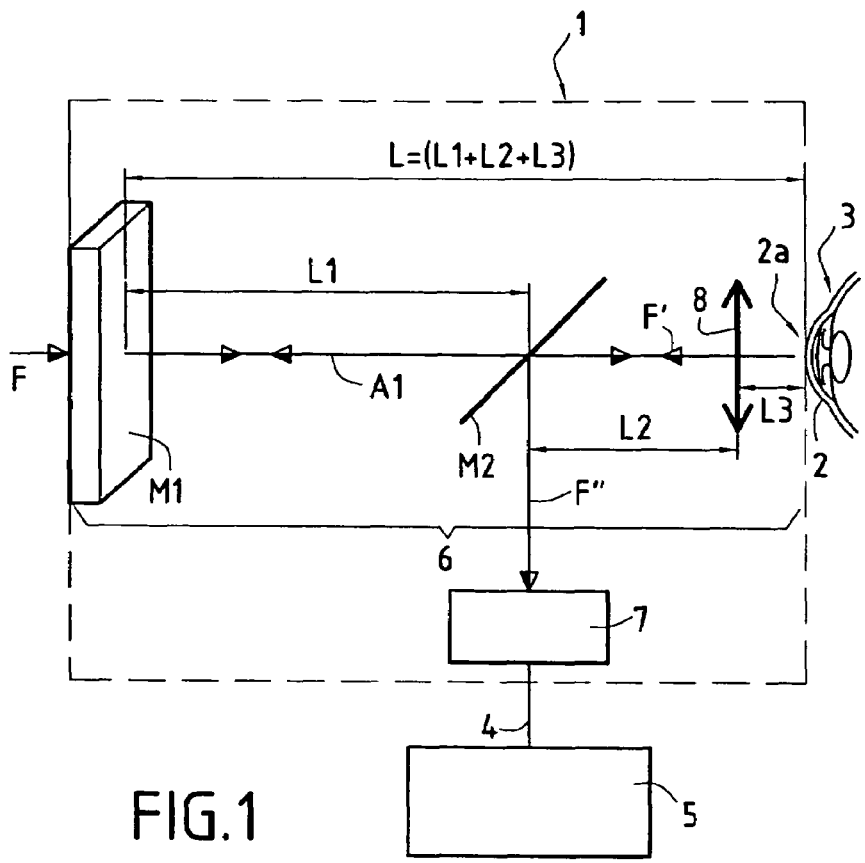
FIG. 1 is a diagram showing the principle of apparatus in accordance with the invention for measuring at least one natural frequency of vibration of an eye, thereby measuring its intraocular pressure (IOP)

The apparatus of FIG. 1 comprises:
a device 1 that enables vibration of the cornea 2 of an eye 3 to be detected optoelectronically by laser interferometry, and that delivers a time-domain electrical signal 4 characteristic of the variation in the amplitude of the vibration of the cornea 2 over time; and
an electronic system 5 for processing the signal, which system is designed initially to compute the frequency spectrum of the time-domain signal 4, e.g. by computing the Fourier transform of the signal 4, and secondly to determine the frequency of at least one natural mode of vibration of the eye from said frequency spectrum.

The contribution of the invention lies essentially in the detection device 1, which is described in detail below. The two above-mentioned computation steps performed by the electronic system 5 and the means needed to implement them are known to the person skilled in the art of signal processing and they are not described in detail in the present description.

Figure 2:
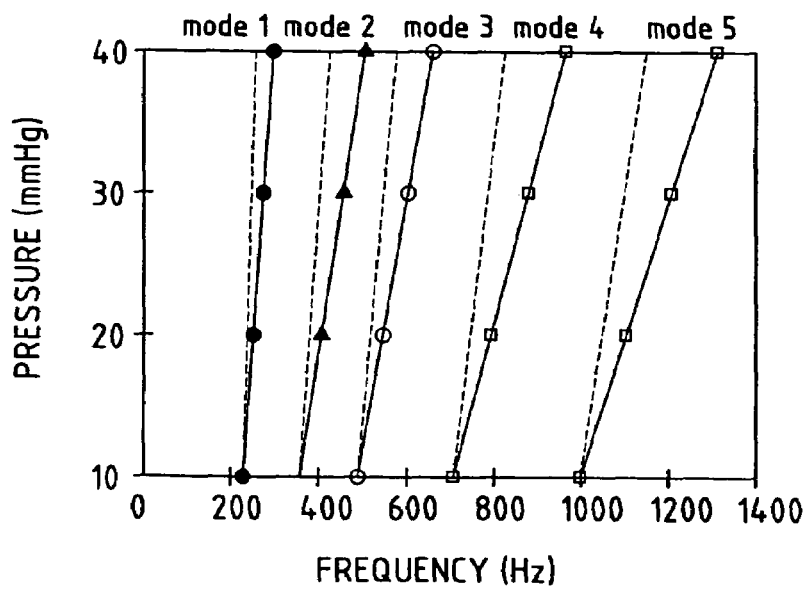
FIG. 2 shows a (known) example of variation in the frequencies of various natural modes of vibration of an eye as a function of its intraocular pressure.
Figure 3:
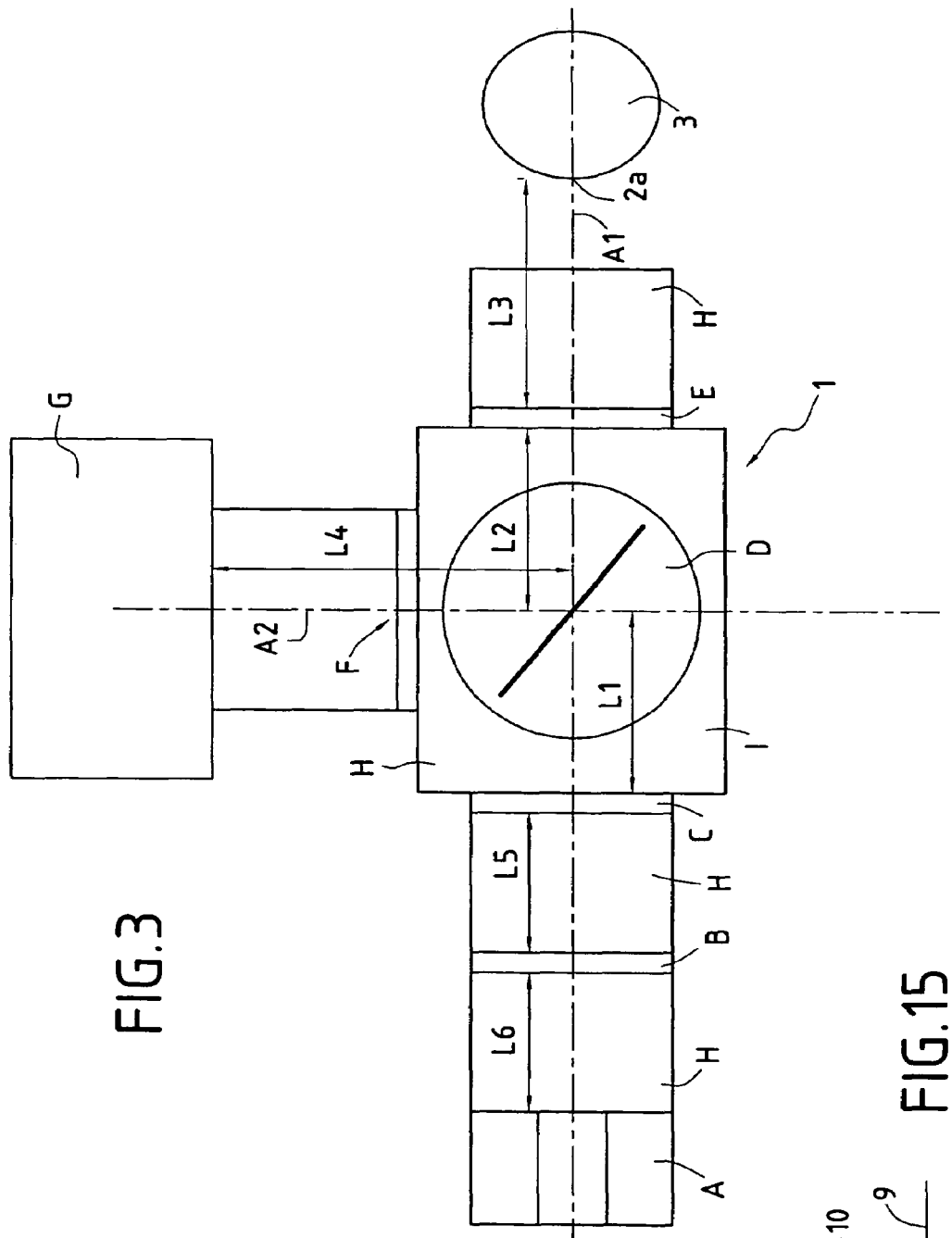
FIGS. 3, 4, 5, and 6 show an embodiment of a detection device of the invention in the form of assembled-together modules.

Prior to describing the detection device 1, it is recalled that the eye can be modelled as a spherically-shaped heterostructure characterized by coefficients of elasticity, viscosity, and impedance. If the eye is mechanically excited in a manner suitable for setting it into vibration, it is possible to excite the natural frequencies of vibration of the heterostructure. These natural modes of vibration have been calculated by modeling the eye mathematically and they make it possible to quantify variations in natural frequency as a function of intraocular pressure. By way of example, accompanying FIG. 2 shows the variation in the frequency of the various natural modes of vibration as a function of intraocular pressure for an eye modelled mathematically by means of a linear model (dashed line curves) or by means of a non-linear model (continuous line curves). It is consequently already known that measuring the frequency of vibration of at least one natural mode of vibration of the eye gives access to a measurement of its intraocular pressure on the basis of calibration that has been performed using prior techniques. It is preferable to measure the frequencies of vibration of the higher modes, and in particular of mode 5 in FIG. 2. Such measurement of intraocular pressure can be used in diagnosing ophthalmological pathologies, with the main pathology being glaucoma of the eye.

Device for Optoelectronic Detection by Laser Interferometry

With reference to FIG. 1, and in accordance with, an essential characteristic of the invention, the detection device 1 comprises an optical portion 6 which, once positioned relative to the eye, forms a Fabry-Perot interferometer having a wave reflection cavity with one of its two ends constituted by the outside surface 2a of the cornea 2 of the eye, and an optoelectronic detector 7 for detecting the intensity I of the wave output by the interferometer 6 and for delivering the above-mentioned electrical signal 4 as a function of said intensity.

With reference to FIGS. 1 and 3 to 6, in a particular variant embodiment, the detection device 1 is made up of nine modules A to I.

Module A: this module comprises a laser diode of wavelength $\lambda$ (e.g. equal to 635 nanometers (nm)) fitted with a system for stabilizing temperature and power (1.9 milliwatts (mW)). The laser diode includes a collimating optical system for limiting the divergence of the laser beam. It can be powered at 4.5 volts (V) using a battery or at 5 V using an external power supply, and its power supply current is limited to 60 milliamps (mA).

Module B: this module is formed by a quarterwave plate (not shown in FIG. 1) serving to polarize the radiation from the laser diode circularly.

Module C: comprises a plane mirror M1 whose reflection and transmission coefficients $R_1$ and $T_1$ are equal respectively to 98% and 2% of intensity. It serves:
  to limit loss of energy from the Fabry-Perot cavity due to the low coefficient of reflection on the eye ($R_3$: 2.5%), and thus to improve the contrast of the interferometer system; and
  to limit the power of the laser diode to (19.73±0.01) microwatts ($\mu W$) (value measured behind the mirror) in order to be able to satisfy the standards for power acceptable on the eye.

Module D: comprises a splitter mirror M2 whose reflection and transmission coefficients $R_2$ and $T_2$ are equal respectively to 40% and 60% of intensity. This splitter mirror M2 enables the power of the laser diode to be reduced a second time so as to bring it to 12.8 μW (value measured after passing through M2).

Module E: is formed by a plano-convex correction lens 8 of focal length $\underline{f}$ having a value more particularly of 30 mm. It serves to correct the divergence caused by the curvature of the cornea of the eye. Focal length is selected as a function of reducing the sensitivity to lateral misalignment of the eye relative to the optical axis of the interferometer system. Furthermore, the lens preferably possesses antireflection treatment at the wavelength of the laser so as to avoid parasitic reflections on the lens which could give rise to a dual-cavity phenomenon.

Module F: this module constitutes an interference filter (not shown in FIG. 1). It is a dielectric plate having partially-reflecting parallel faces which transmit only a band of the spectrum in the incident radiation. More particularly, in one embodiment, this plate serves to transmit a spectrum band that is 10 nm wide and that is centered on the wavelength of the laser, thus isolating the detector 7 from all light radiation (e.g. lighting) other than the radiation from the laser diode in the module A. This filter preferably possesses antireflection treatment at the laser wavelength (635 nm) on its opposite face (its face beside the detector 7) in order to avoid any parasitic reflection between the surface of the detector 7 and the surface of the interference filter.

Module G: this forms the above-mentioned optoelectronic detector 7. More particularly, the detector is an avalanche detector presenting the following operating characteristics, given for an operating temperature of 25° C. with a power supply of ±12 V.

| Parameters | Values | Units |
|---|---|---|
| Diameter of the active surface of the detector | 3.0 | Mm |
| Spectrum response | 400 to 1000 | Nm |
| Sensitivity peak | 800 | Nm |
| Photosensitivity (800 nm, gain = 1) | 0.5 | A/W |
| Stability of gain to temperature (25° C. ± 10° C., gain = 30) | ±2.5 typ. ±5 max. | % |

| Parameters | Min. | Typ. | Max. | Units |
|---|---|---|---|---|
| High cutoff frequency | 9 | 10 | — | kHz |
| Low cutoff frequency | — | DC | — | kHz |
| Noise equivalent power at 800 nm (NEP) | — | 0.02 | 0.04 | pW/Hz$^{1/2}$ @ 10 MHz |
| Resistance of equivalent circuit | — | 10 | — | MΩ |
| Photoelectric sensitivity (800 nm and gain = 30) | -1.4 | -1.5 | -1.6 | $10^6$ V/W |
| Maximum input intensity | 0.05 | 0.06 | — | μW |
| Minimum detectable intensity | — | 0.005 | 0.01 | nW |

It performs integration over a large circular area (diameter 3.0 mm) in order to remedy the problem of the eye being optically out of alignment. It possesses a passband of 100 kHz and it can measure a limiting power of $0.005 \times 10^{-9}$ W at a wavelength of 800 nm.

Module H: (FIG. 4) constitutes a tubular mount comprising an outer tube H1 having an inner tube H2 inserted therein and serving to support an optical system O by means of a clamping screw V. A tubular mount H is designed to be assembled with other mounts-of-the-same type and thus to enable a more complex structure to be built up while protecting the various optical units 0. To make up the detection device 1, four tubular mounts H are used, serving to house respectively: the quarterwave plate (above-mentioned module B); the plane mirror M1 (module C); the plano-convex lens 8 (module E); and the interference filter (module F).

Module I: (FIG. 5) this module serves to assemble together the tubular mounts H along two perpendicular axes, and itself serves as a housing for the splitter mirror M2.

Figure 6:
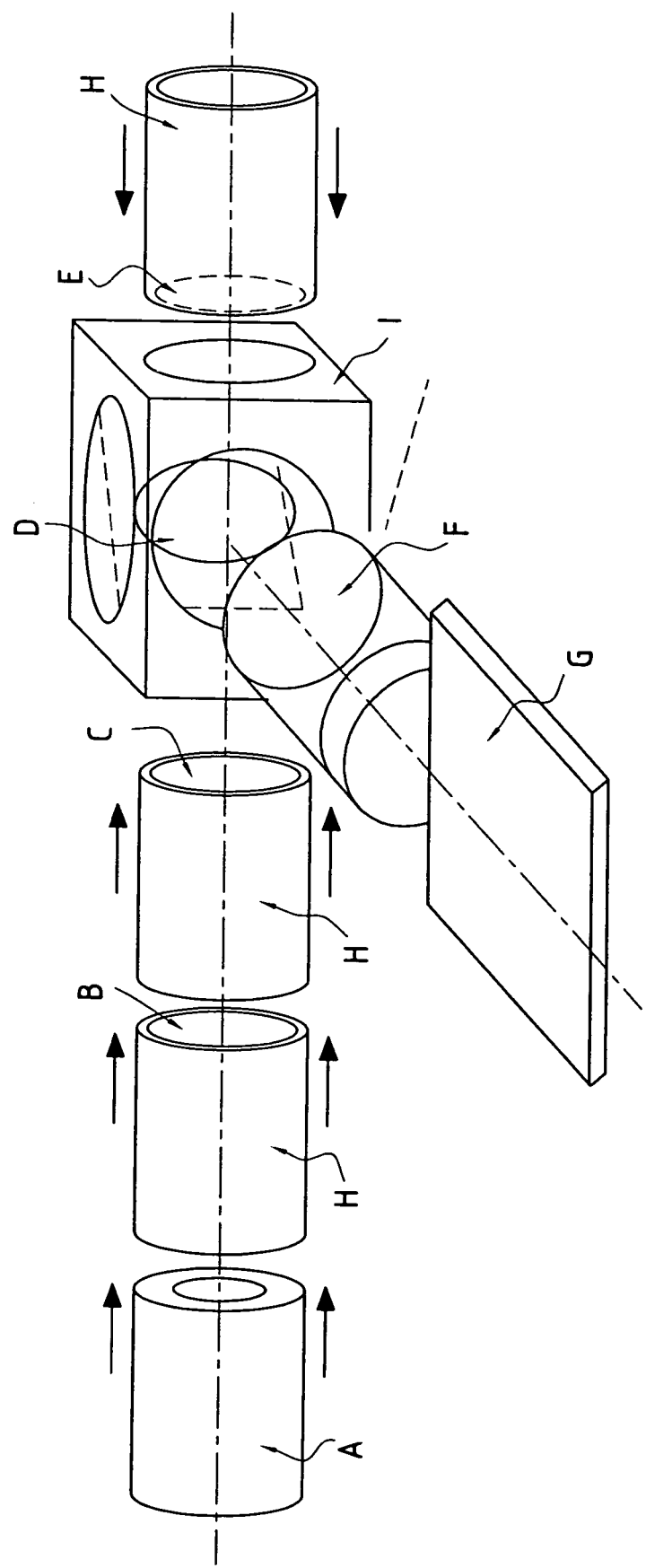

FIG. 6 shows how the various modules are assembled to one another in order to constitute the detection device 1. With reference to FIGS. 1 and 6, the detection device 1 forms an optical system having a main optical axis A1, and a secondary optical axis A2 oriented at 90° by using the splitter mirror M2. The laser diode (module A), the quarterwave plate (module B), the plane mirror M1, the splitter mirror M2 (module C), and the plano-convex lens 8 (module E) are aligned in fixed and precise manner and are centered on the main optical axis A1. The splitter mirror M2 (module D), the interference filter (module F), and the detector 7 (module G) are aligned in fixed and precise manner and are centered on the secondary optical axis A2. In a particular embodiment given purely by way of indication, the distances $L_1$, $L_2$, and $L_5$ and $L_6$ (FIG. 3 and FIG. 1) are equal to 2.5 centimeters (cm), and the distance $L_4$ is 5 cm.

In order to detect the natural modes of vibration of an eye 3 by means of the above-described detection device 1, the center of the cornea 2 of the eye 3 is put substantially into alignment on the main optical axis A1 (see discussion below about the lateral sensitivity of the device) by positioning the eye longitudinally at a predetermined distance $L_3$ (see discussion below about the longitudinal sensitivity of the device) in such a manner that the module I and the module H (serving as a housing for the plano-convex lens 8) form a Fabry-Perot cavity on the main optical axis A1, with one of the reflecting faces on said main optical axis being constituted by the plane mirror M1 and with the other, opposite reflecting face being constituted by the cornea 2 of the eye 3, the length L (i.e. the distance between the cornea and the plane mirror M1) of said Fabry-Perot cavity is variable, depending on the amplitudes of vibration of the cornea 2 of the eye 3.

With reference to the theoretical diagram of FIG. 1, in operation the incoming laser beam F (after being circularly polarized by the above-mentioned quarterwave plate) is injected into the Fabry-Perot cavity by passing through the mirror M1, and it passes through the splitter mirror M2 before reaching the surface 2a of the cornea 2. A fraction of this incident beam is reflected by the cornea back to the splitter mirror M2 in the form of a return beam F'. On reaching the splitter mirror M2, this return beam F' is deflected in part through 90° by the splitter mirror M2 so as to form the outlet beam F"; the remainder of the return beam F' is transmitted through M2 and reaches the plane mirror M1 where it is subjected to reflection, etc. . . . .

The intensity transmitted by the Fabry-Perot cavity of variable length L, i.e. the intensity I of the outlet beam F" relative to the (known) intensity $I_0$ of the incident laser beam F is given by the following formula:

$$\frac{I}{I_0} = \frac{T_1 R_2}{T_2 R_1 (1 - T_2 \sqrt{R_1 R_3})^2} * \frac{1}{1 + \frac{4T\sqrt{R_1 R_3}}{\left(1 - T_2 \sqrt{R_1 R_3}\right)^2} \sin^2 \frac{2\pi}{\lambda} L} \quad (1)$$

The intensity I at the outlet from the Fabry-Perot cavity (signal 4 delivered by the optoelectronic detector 7) varies periodically as a function of the variable length L of the cavity.

For integer multiples of $\lambda/2$ (where $\lambda$ is the wavelength of the laser), the intensity is at a maximum and is given by the following formula:

$$I_M = I_0 * \frac{R_2 T_1}{R_1 T_2 (1 - T_2 \sqrt{R_1 R_3})^2} \quad (2)$$

For integer multiples of $\lambda/2$ plus a half, the intensity is at a minimum and is given by the following formula:

$$\frac{I}{I_m} = I_0 * \frac{R_2 T_1}{R_1 T_2 (1 - T_2 \sqrt{R_1 R_3})^2} * \frac{1}{1 + \frac{4T_2 \sqrt{R_1 R_3}}{\left(1 - T_2 \sqrt{R_1 R_3}\right)^2}} \quad (3)$$

Thus, the period of the transfer function of the Fabry-Perot interferometer corresponds to half the wavelength of the laser beam injected into the cavity. In other words, for a laser diode of wavelength $\lambda$, the interferometer can measure variations in the length L of the order of $\lambda/2$.

The vibration of the cornea 2 can be considered as being a damped sinusoidal oscillation (in order to take account of the constraint exerted by the orbit of the eye and the constraint exerted by the muscles associated with the eye). Under such circumstances, the length L of the cavity is of the form:

$$L(t) = L_0 + l \cdot e^{-t/c} \cdot \sin(wt) \quad (4)$$

In formula (4):
  l represents the amplitude of the vibration of the surface 2a of the cornea 2;
  w is the vibration frequency of the eye; and
  c is the damping coefficient.

Figure 7:
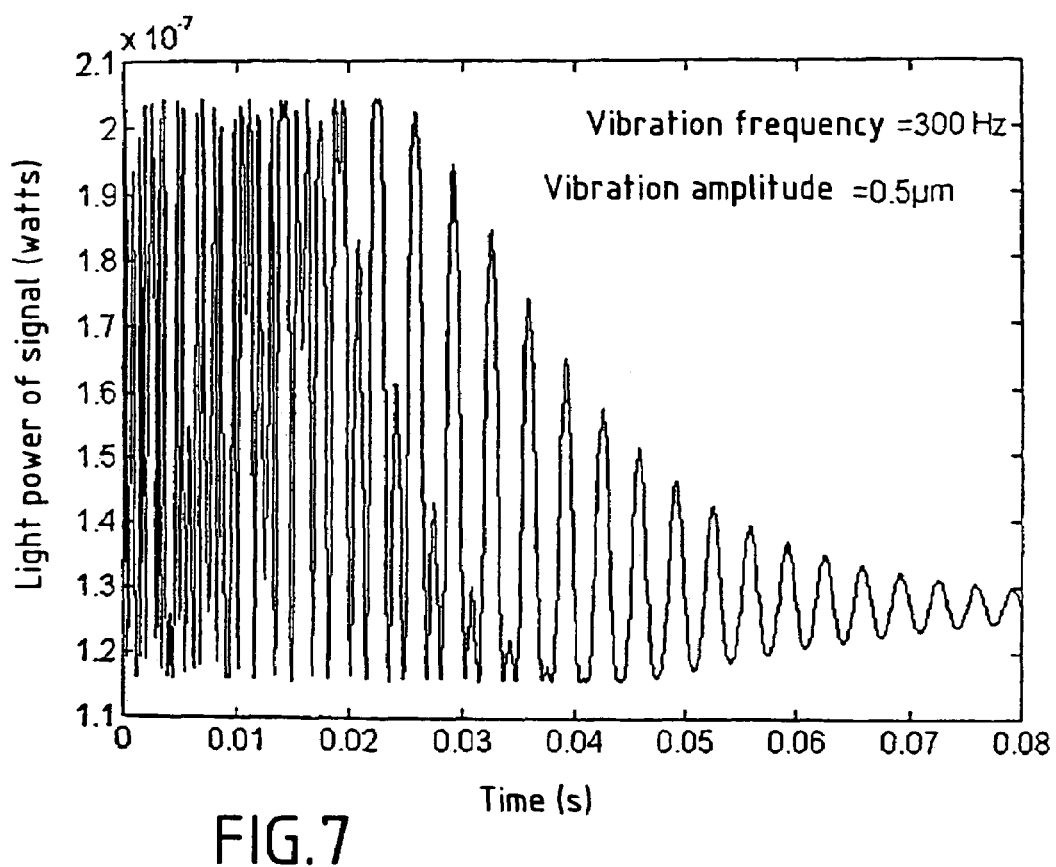
FIG. 7 shows a particular example of the signal measured by the detector of the invention, representative of a natural frequency of vibration of the eye at 300 hertz (Hz)

From the above considerations, it results that the intensity I output by the Fabry-Perot cavity and measured by the optoelectronic detector 7 (signal 4) passes through a succession of extremums at a certain speed that is characteristic of the frequency of vibration of the cornea. As an indication, one particular example of the signal 4 measured by the detector is given in FIG. 7 and represents a natural frequency of vibration of the eye of 300 Hz with the initial amplitude of cornea oscillation prior to damping being 0.5 µm.

Figure 8:
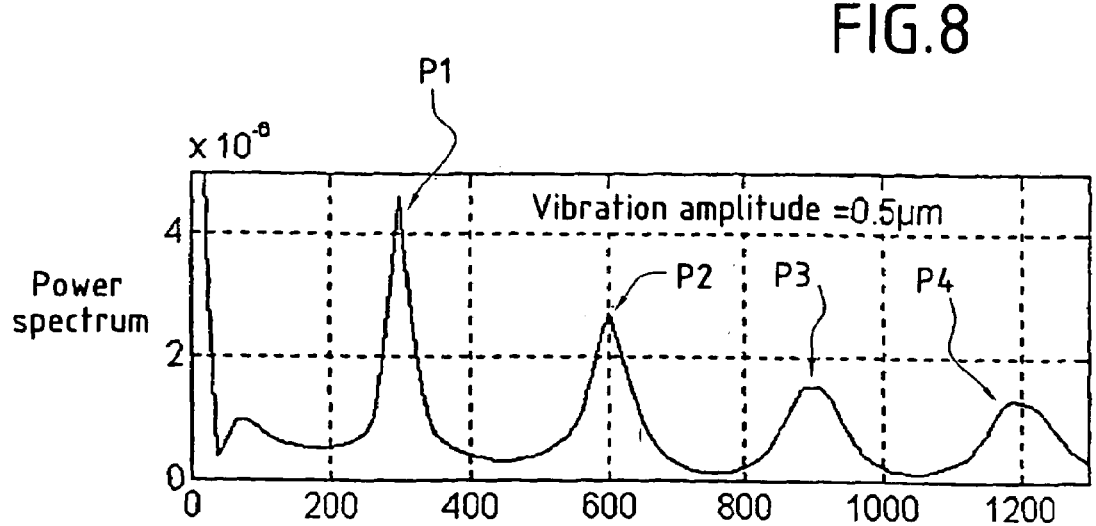
FIG. 8 shows the power spectrum of the FIG. 7 signal after applying a Fourier transform.

To obtain the vibration frequency of the cornea, it suffices to perform the Fourier transform on the signal 4 (first step performed by the electronic system 5 in FIG. 1). This provides a power spectrum for the signal 4, of the type shown in FIG. 8. In this spectrum there can be seen a main peak $P_1$ corresponding to the frequency of vibration of the cornea 2, together with harmonics of this frequency as characterized by peaks $P_2$, $P_3$, $P_4$ of lower intensity.

Since the eye is a non-stationary element of the Fabry-Perot cavity, alignment of the eye constitutes a parameter that varies from one measurement to another and it is therefore necessary to define variation limits that are not to be exceeded in order to obtain measurements of the natural modes of vibration of the eye. The sensitivity of the above-described detection device 1 to longitudinal misalignment and to lateral misalignment are dealt with briefly below.

Longitudinal Sensitivity

The idea is to define a range of stability which makes it possible to guarantee that the beam is refocused on itself in the cavity along the main optical axis A1. For longitudinal stability, consideration should be given to the portion constituted by the plane mirror M1 and the system comprising the eye and the lens 8. Given that only the eye-lens distance varies in the detection device 1, a study of longitudinal stability consists in determining the capability of the Fabry-Perot cavity (as formed by the plane mirror M1 and the system comprising the eye and the lens 8) to confine radiation as a function of the distance between the eye and the lens 8 (distance $L_3$ in FIG. 1).

A Fabry-Perot cavity is longitudinally stable when after $\underline{n}$ round trips the beam is refocused on itself. Modeling the eye as a diverging spherical mirror having a radius of curvature R, the transfer matrix of the Fabry-Perot cavity for calculating the coordinates of the light ray after $\underline{n}$ round trips through the cavity as a function of its initial coordinates on entering the cavity is as follows:

$$M = \frac{1}{\sin\theta} \begin{bmatrix} A\sin n\theta - \sin(n-1)\theta & B\sin\theta \\ C\sin\theta & D\sin n\theta - \sin(n-1)\theta \end{bmatrix} \quad (5)$$

in which firstly:

$$A = \left(1 - \frac{L_3}{f}\right) * \left[\left(1 - \frac{L}{f}\right)\left(1 + \frac{2L_3}{R}\right) + \frac{2L}{R}\right] - \quad (6)$$
$$\frac{1}{f}\left[L_3\left(1 - \frac{L}{f}\right) + L\right]$$

$$B = \left[\left(1 - \frac{L}{f}\right)\left(1 + \frac{2L_3}{R}\right) + \frac{2L}{R}\right]\left[L\left(1 - \frac{L_3}{f}\right) + L_3\right] + \quad (7)$$
$$\left(1 - \frac{L}{f}\right)\left[L_3 - \left(1 - \frac{L}{f}\right) + L\right]$$

$$C = \left[-\frac{1}{f}\left(1 + \frac{2L_3}{R}\right) + \frac{2}{R}\right]\left(1 - \frac{L_3}{f}\right) - \frac{1}{f}\left(1 - \frac{L_3}{f}\right) \quad (8)$$

$$D = \left[L\left(1 - \frac{L_3}{f}\right) + L_3\right]\left[\frac{2}{R} - \frac{1}{f}\left(1 + \frac{2L_3}{R}\right)\right] + \left(1 - \frac{L_3}{f}\right)\left(1 - \frac{L}{f}\right) \quad (9)$$

And secondly:

$$\cos\theta = \frac{1}{2}(A + D) \quad (10)$$

It is recalled that the above-mentioned distances L and $L_3$ are those given in FIG. 1 and that the parameter $\underline{f}$ represents the focal length of the lens 8.

In order to ensure that the cavity is stable, $\theta$ must be real, and this stability condition is equivalent to the condition: $|A+D| \leq 2$.

Figure 9:
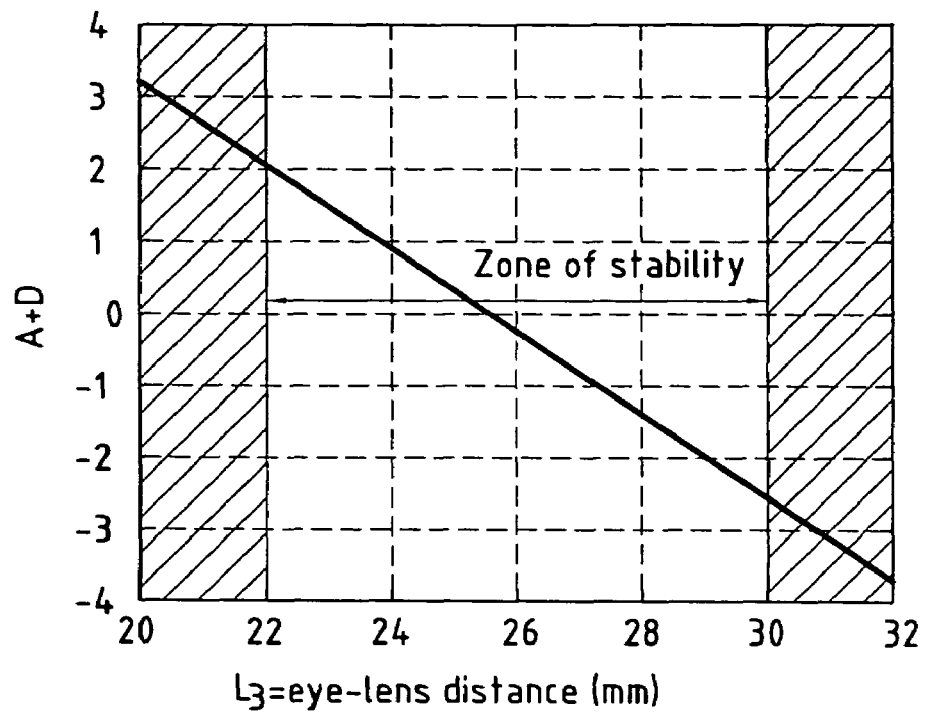
FIG. 9 is a graph for determining the longitudinal sensitivity of the detection device in one particular case.

FIG. 9 plots the curve of A+D as a function of the eye-to-lens distance $L_3$ for a lens 8 having a focal length $\underline{f}$ of 30 mm. From this graph it can be seen that in this particular case the zone of stability is obtained when $L_3$ lies in the range 22 mm to 30 mm. For proper operation of the detection device 1, it therefore suffices in this case to make sure that the eye is maintained at a distance $L_3$ lying within the above-specified stability range.

Lateral Sensitivity

It is essential for the eye to be in lateral alignment with the main optical axis A1 of the Fabry-Perot cavity in order to obtain an interference signal at the detector 7. The purpose of the following study on lateral sensitivity is firstly to determine a limiting threshold on acceptable lateral misalignment and secondly to devise a system for aligning the eye that takes account of this lateral sensitivity.

Figure 10:
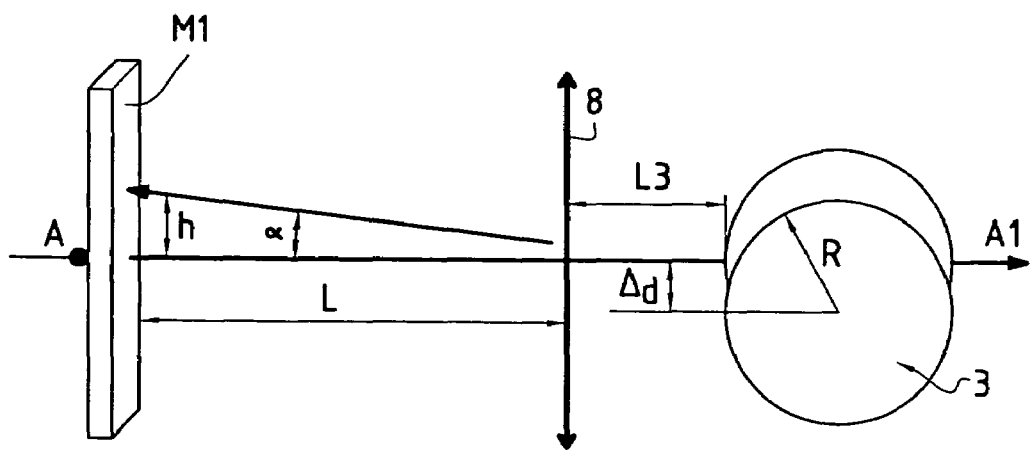
FIG. 10 is a simplified optical diagram for showing the effects of the eye being laterally out of alignment by $\Delta_d$.
Figure 11:
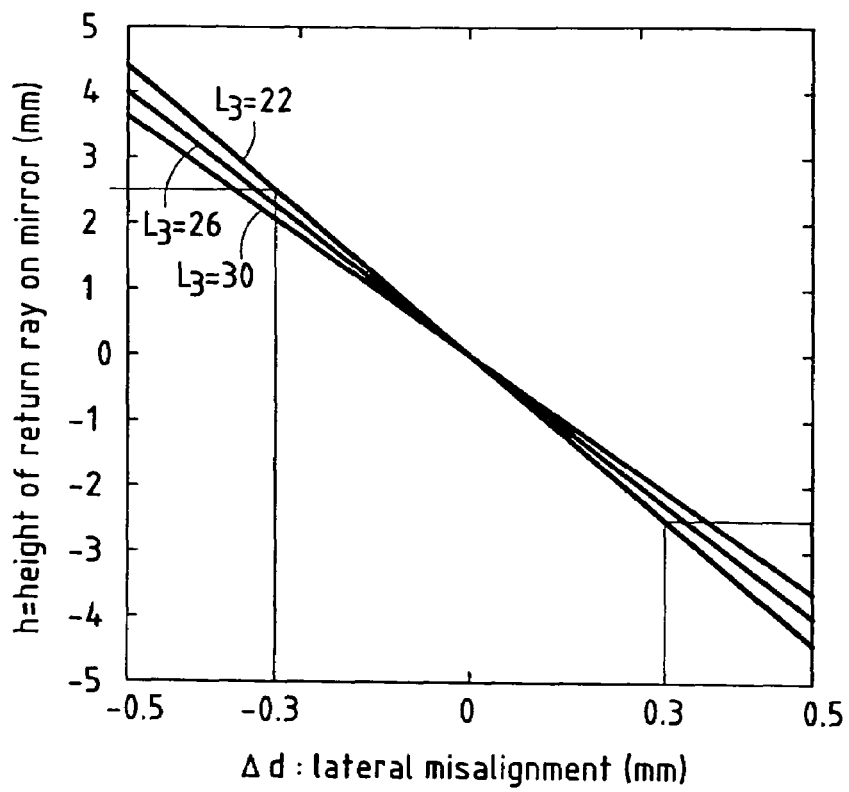
FIGS. 11 and 12 show respectively the height $\underline{h}$ at the angle $\alpha$ (for one round trip of the light beam through the Fabry-Perot cavity) as a function of the lateral misalignment $\Delta_d$.
Figure 12:
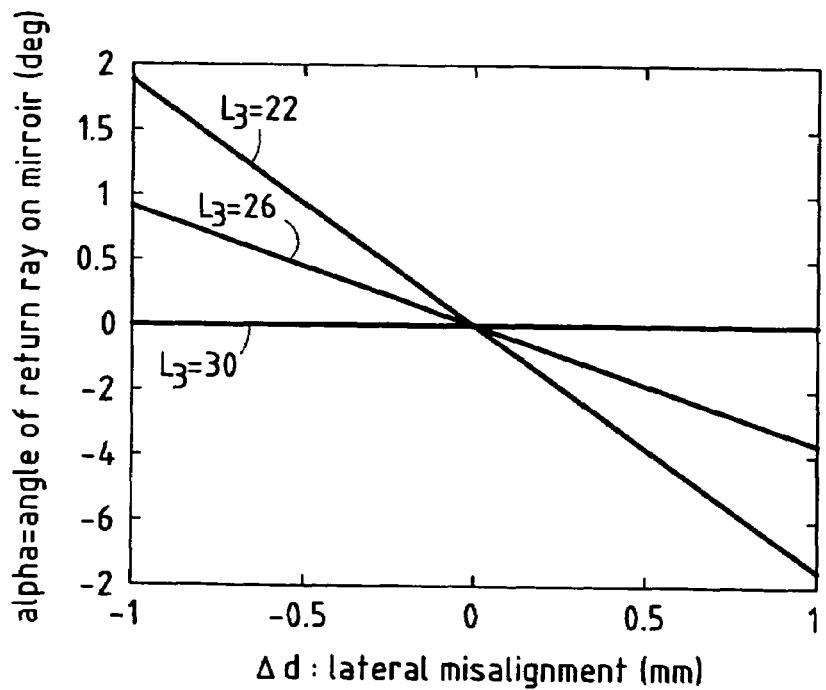
Figure 13:
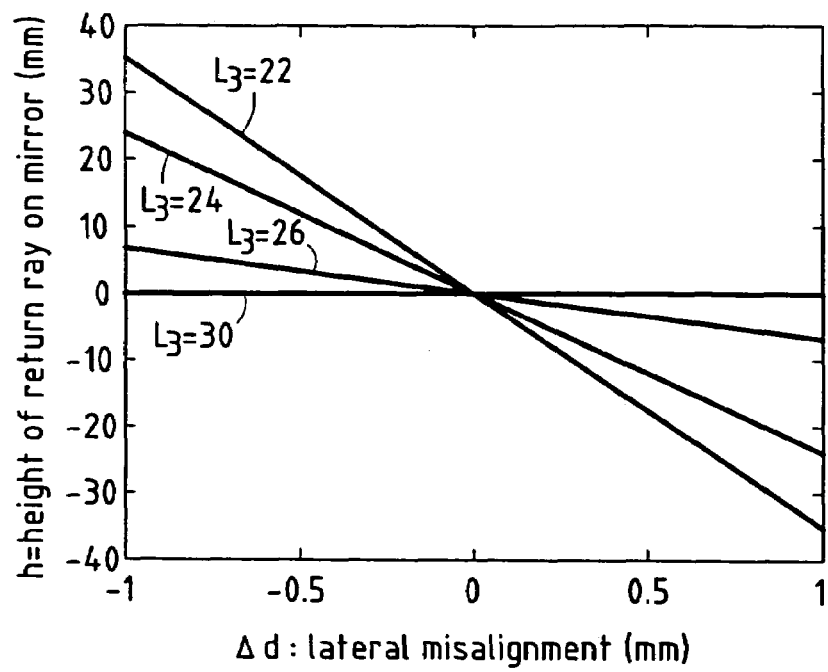
FIGS. 13 and 14 are comparable respectively with FIGS. 11 and 12, but relate to two round trips of the light beam in the Fabry-Perot cavity.
Figure 14:
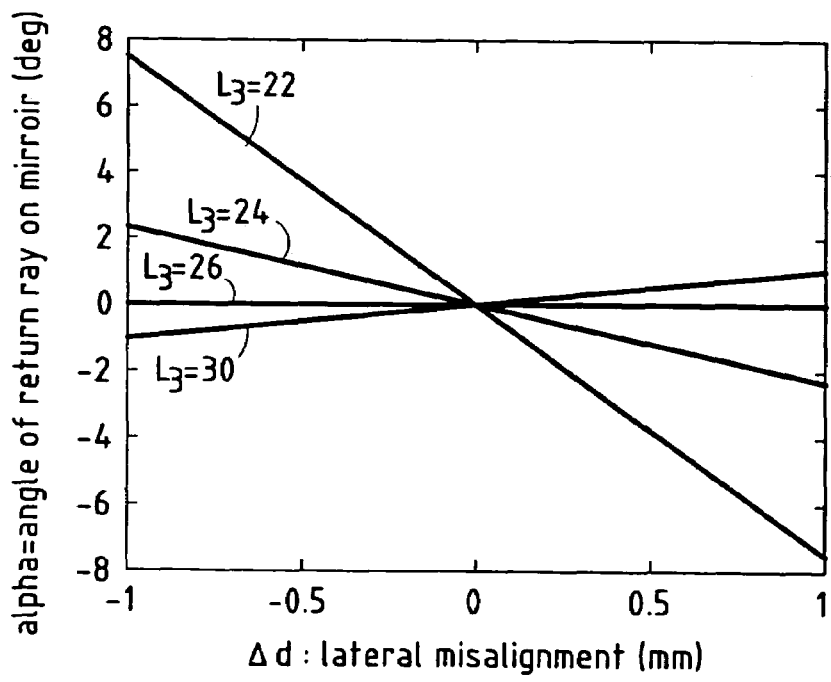

With reference to the optical diagram of FIG. 10, the parameter characterizing lateral misalignment is the distance $\Delta_d$, which has an influence on the height $\underline{h}$ and on the angle $\alpha$ of the return ray at the plane mirror M1. FIGS. 11 and 12 show respectively the height $\underline{h}$ and the angle $\alpha$ after one round trip of the light beam through the cavity as a function of lateral misalignment $\Delta_d$ from the optical axis A1 for a focal length $\underline{f}$ of 30 mm, with this being shown for a plurality of distances $L_3$ between the eye and the lens 8 given in mm. FIGS. 13 and 14 are comparable respectively with FIGS. 11 and 12 but they apply to two round trips of the light beam through the cavity. In practice, there is no need to take more than two round trips of the beam into consideration since beyond that the amplitudes of the interfering waves become negligible.

The results of FIGS. 11 to 14 show that the detection device 1 is very sensitive to lateral misalignment. A lateral misalignment of the eye from the optical axis by 0.5 mm causes the return beam to diverge through an angle lying in the range 2° to 0°, depending on where the eye is placed in terms of distance $L_3$ from the lens 8 lying in the range 22 mm to 30 mm. This divergence leads to the beam having a height $\underline{h}$ at the plane mirror M1 that can be as great as 4 mm. It can be considered that the cavity is stable providing the height $\underline{h}$ is less than the width (commonly referred to as the "waist") of the beam in the cavity. Consequently, in the particular case shown in FIGS. 11 to 14 for a beam having a mean width of 3 mm, it can be considered that the device is stable up to a lateral misalignment $\Delta_d$ of 0.3 mm, and that beyond that the Fabry-Perot cavity becomes unstable.

Optimizing the Detection Device to Reduce Sensitivity to Lateral Misalignment

A reduction in lateral sensitivity can be obtained firstly by reducing the length L of the Fabry-Perot cavity. A shorter cavity serves to limit the effects of the divergence of the return beam (parameters $\underline{h}$ and $\alpha$) induced by the lateral misalignment of the eye.

A greater reduction in lateral sensitivity can also be obtained by selecting a lens 8 that possesses a short focal length $\underline{f}$. Calculations performed for a focal length of 20 mm (instead of 30 mm as above) reveal a reduction in the height $\underline{h}$ of more than 1 mm for one round trip and of more than 5 mm for two round trips. Thus, by selecting a focal length of 20 mm for the lens 8, it is possible to align the eye relative to the optical axis with the less-constraining precision of 0.5 mm. Conversely, in order to illustrate the importance of the focal length of the lens 8 on lateral sensitivity, if the detection device 1 is fitted with a lens 8 having a focal length of 50 mm, the alignment of the eye with the optical axis needs to be achieved with precision smaller than 0.15 mm.

In conclusion, by a suitable selection of short focal length $\underline{f}$ or the lens 8 (e.g. 20 mm) and a short length L for the cavity, lateral sensitivity of the device is optimized.

Figure 15:
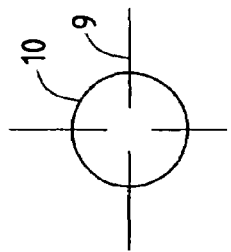
FIG. 15 shows an example of a reticle used in a first variant embodiment for achieving lateral and longitudinal alignment of the eye relative to the main optical axis of the detection device.
Figure 4:
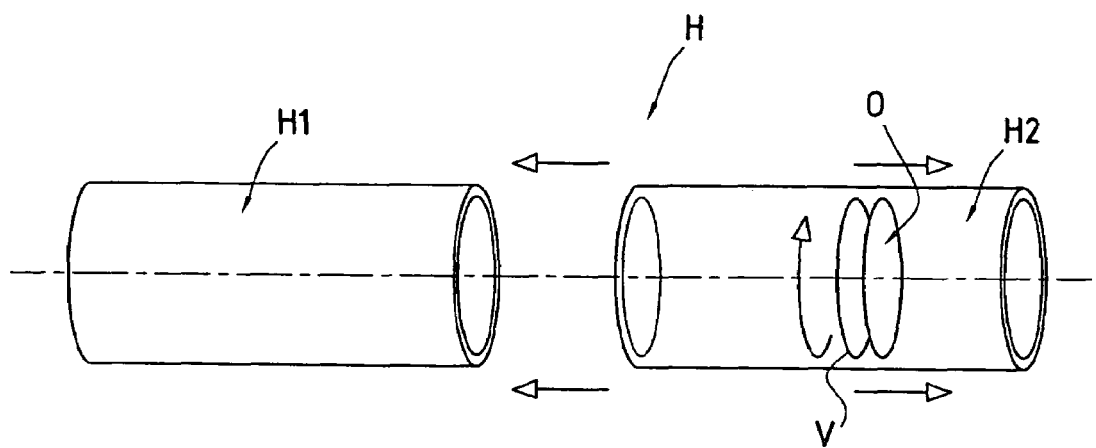
Figure 5:
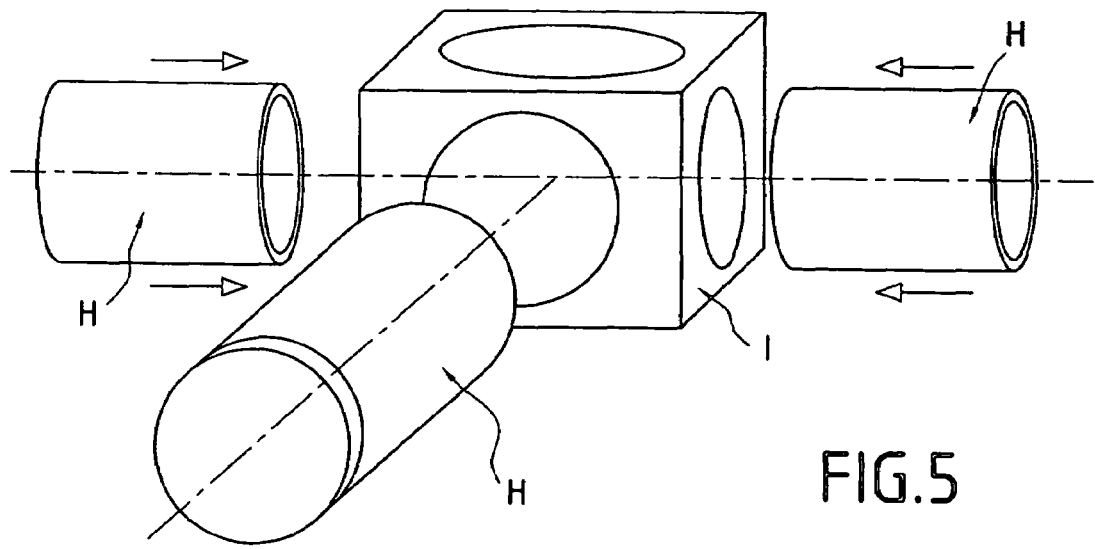

Improvement of the Detection Device 1: a Reticle for Performing Lateral and Longitudinal Alignment FIG. 15 shows a reticle pattern at life size comprising a cross 9 used for laterally aligning the eye with the optical axis, and a circle 10 used for aligning the eye longitudinally relative to the lens 8 (distance $L_3$). This reticle is placed in the Fabry-Perot cavity between the reflecting element M1 and the lens 8, and more particularly between the splitter mirror M2 and the lens 8, preferably in the focal plane of the lens 8 so that observing the image of the reticle by eye through the lens 8 is as little tiring as possible, given that a normal eye has no need to accommodate. Since the reticle lies on the path of the beam it is made on a transparent plate possessing a coefficient of reflection at the wavelength $\lambda$ of the laser that is as small as possible so as to avoid decreasing the intensity transmitted by the cavity. For this purpose, the plate may be treated for example with a coating that is non-reflecting at the laser wavelength.

Lateral Alignment

When the eye observes the virtual image of the cross 9 of the reticle through the lens 8, the branches of the cross deform when the eye is no longer in alignment with the optical axis of the lens 8 (i.e. the optical axis A1 of the cavity). This deformation increases with decreasing focal length $\underline{f}$ of the lens.

Longitudinal Alignment

The minimum distance $L_3$ (bottom value of the above-defined longitudinal range of stability) is determined by the length of the tubular mount in which the lens 8 is inserted. For longitudinal alignment purposes it therefore suffices to be able to increase the distance $L_3$ (i.e. the distance between the eye and the lens 8) to the maximum authorized value (30 mm in the above example) for the longitudinal stability range of the device. For this purpose, the diameter of the circle 10 of the reticle is determined as a function of said maximum authorized value for $L_3$ so that the circle is observable by the eye 3 through the lens 8 when the eye is situated at a distance $L_3$ from the lens 8 that is less than the maximum value for the stability range. By way of example, for a maximum value of 30 mm, the diameter of the circle 10 should be 1 cm.

Implementing the Detection Device

Using the reticle, the first step is to align the eye laterally relative to the optical axis A1 of the Fabry-Perot cavity (with lateral alignment being corrected until the cross 9 of the reticle no longer appears to be deformed) and the eye is aligned longitudinally relative to the lens (by correcting the distance $L_3$ until the eye can see the circle 10 of the reticle). In order to correct the position of the eye, the device may be fixed on apparatus enabling the position of the device 1 to be adjusted accurately in three-dimensional space and including a system for holding the head of the patient in said space in order to avoid any parasitic displacement other than displacement of the detection device (for example a chin-rest with a control bar for moving the detection device 1). Nevertheless the invention is not limited to this; it is also possible to envisage a detection device of outpatient type, given specifically that the reticle makes it easy for an untrained person to validate lateral and longitudinal alignments of that person's own eye relative to the optical axis A1 of the device.

Once the eye has been aligned longitudinally and laterally, the eye is excited mechanically in order to set it into vibration. This excitation may be of the harmonic type, or preferably of the impulse type, given that the detection device can be used with both of those two excitation methods. In the first case (harmonic method), the eye is excited mechanically, e.g. by means of a sound wave transmitted to the eye cavity, while sweeping the wave in frequency. The harmonic method nevertheless suffers from the drawback of being lengthy, and traumatizing for the patient. Consequently, it is preferred to use the impulse method which consists in subjecting the eye to a short impulse that can be considered as being a Dirac delta impulse covering the entire spectrum of excitation frequencies. Such impulse type excitation can be obtained for example, by a short and light impact against the skull of the patient close to the eye socket. In a manner that is more advantageous and unexpected it has been found in accordance with the invention and verified that such an impulse can be obtained merely by blinking an eyelid, or possibly by a plurality of short and repeated blinks of the eyelid. This can be explained by the fact that during a blink the eyelid rubs against the anterior face of the eye (cornea, bulbar conjunctiva, and indirectly the sclera). This short rubbing can thus be considered to be an excitation of the eye by means of a mechanical impulse.

The invention is not limited to the particular detection device described above with reference to the accompanying figures. In general, the plano-convex correction lens 8 could be replaced by any other converging lens. In another variant embodiment, the mirror M1 could be replaced by a plano-convex lens whose plane face is treated so as to enable the laser beam to be reflected in the Fabry-Perot cavity. In another variant embodiment, the Fabry-Perot cavity could be made by means of an optical fiber; more particularly, the optical fiber should be fitted at one of its ends with a microlens performing the same function as the correction lens 8 of the above-described detection device, the optical fiber including a Bragg grating, for example, performing the same function as the mirror M1. This variant with an optical fiber makes it possible advantageously to devise a detection device that is miniaturized, suitable for outpatient work.

Figure 16:
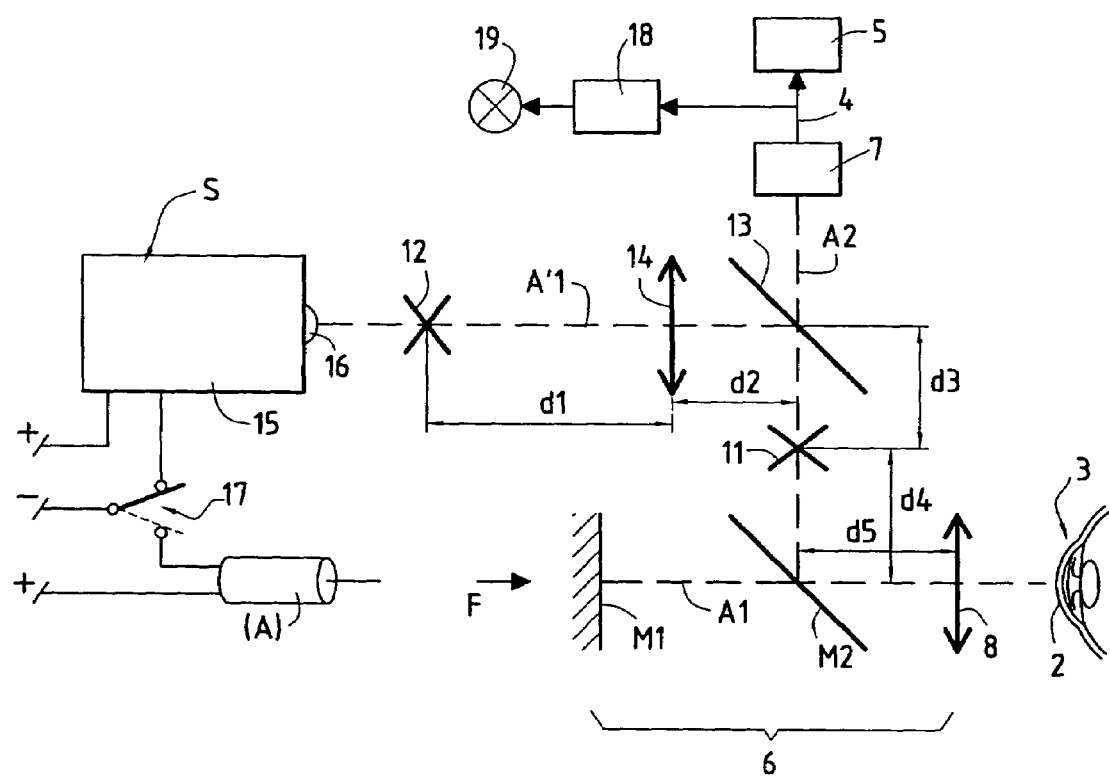
FIG. 16 is a diagram of another variant embodiment of apparatus of the invention, implementing improved optical means for monitoring lateral and longitudinal alignment of the eye.

FIG. 16 shows a variant embodiment having improved means for monitoring lateral and longitudinal alignment of the eye relative to the main optical axis A1. These improved means comprise:

- a light source S which, once switched on, emits an incoherent beam that is not dangerous to the eye; for example it can be a white light source 15 fitted at its outlet with ground glass 16;
- a semireflecting plate 13 in alignment with the splitter mirror M2 on the secondary optical axis A2, and in alignment with the light source S on an optical axis A'1 parallel to the main axis A1, and making it possible firstly to direct the light beam from the source S towards the splitter mirror M2, said beam then being directed towards the eye along the main optical axis A1 after passing through the lens 8, and which also allows the return beam reflected by the eye to pass through on its way to the detector 7 (secondary optical axis A2);
- a converging lens 14 (e.g. a plano-convex lens) of focal length f', centered on the optical axis A'1 and positioned between the source S and the semireflecting plate 13; and
- two reticles 11 and 12 (or graticules) that are not oriented, e.g. in the form of crosses disposed on either side of the lens 14 and centered on the optical axis of the lens 14, the reticle 11 being more particularly centered on the secondary optical axis A2 between the semireflecting plate 13 and the splitter mirror M2, the reticle 12 being centered on the optical axis A'1 between the source S and the lens 14.

The two reticles 11 and 12 are preferably identical and are positioned at a distance 2f' from the lens 14 (distance $d_1$ for the reticle 12, and optical path $(d_2+d_3)$ for the reticle 11). The reticle 11 is preferably positioned at a distance 2f from the correction lens 8 [FIG. 16, optical path $(d_4+d_5)$]. In the preferred embodiment of FIG. 16, the focal length $f$ of the correction lens 8 is equal to the focal length f' of the lens 14. Nevertheless, this characteristic is not essential.

More particularly, the light source S and the laser diode (module A) are both switched on under the control of a two-position contactor 17: it has a first position (continuous line) in which only the source S is powered; and a second position (dashed line) in which only the laser diode is powered.

Longitudinal and transverse alignment adjustments of the eye are performed making use solely of the light source S, the laser diode not operating during such adjustments.

Adjusting Lateral Alignment of the Eye Relative to the Optical Axis A1

With the light source S powered, both reticles 11 and 12 are illuminated, and lateral alignment of the eye is obtained when the eye 2 sees both reticles 11 and 12 as coinciding.

Longitudinal Alignment Adjustment of the Eye Along the Optical Axis A1

Optimum longitudinal alignment of the eye is obtained when the light intensity detected by the detector 7 is greater than a predetermined threshold, and preferably when it reaches its maximum level. For this purpose, with reference to FIG. 16, a comparator circuit 18 compares the signal 4 delivered by the detector 7 with a preferably adjustable predetermined threshold, and it operates an indicator 19 informing the user that longitudinal alignment is correct (e.g. it lights a light-emitting diode (LED)) when the amplitude of the signal 4 is above the threshold.

Once the eye has been aligned laterally and longitudinally, the user can operate the contactor 17 to put the laser diode into operation to measure IOP. This variant of FIG. 16 makes it possible advantageously to simplify monitoring the adjustment of lateral and longitudinal alignment of the eye prior to taking a measurement, thus making this action possible for a user without requiring assistance from a skilled third party, such as an ophthalmological practitioner, in particular.

In a preferred variant embodiment, the light source S is a white light source. Nevertheless this characteristic is not limiting. It could be a light source that presents a narrow frequency spectrum centered on a given wavelength, and not traumatizing for the eye (e.g. a red source). Under such circumstances, when the optoelectronic detector 7 is fitted upstream with an interference filter (not shown in FIG. 1 or 16), it is appropriate to ensure that the interference filter is suitable for transmitting the radiation coming from the source S.

What is claimed is:

1. A method of detecting at least one natural mode of vibration of an eye by laser interferometry, the method comprising the steps of:
    positioning the eye relative to a detection device so as to co-operate with the device to form a Fabry-Perot cavity having a main optical axis and comprising two opposite reflecting faces on the main optical axis, one of these two faces being constituted by a stationary reflecting element and the other being formed by the cornea of the eye;
    injecting an incident laser beam injected into said cavity, the beam being centered on the main optical axis of the Fabry-Perot cavity, the cornea being aligned laterally and longitudinally relative to the main optical axis in such a manner as to obtain longitudinal interference between the go and the return laser beams reflected between the two reflecting faces of the cavity; and
    using an optoelectronic detector used to detect the intensity I of said interference as a function of time.

2. A method according to claim 1, wherein a converging correction lens is interposed between the eye and the reflecting element, the lens being centered on the main optical axis and serving to reduce sensitivity to lateral misalignment of the eye relative to the main optical axis.

3. A method according to claim 2, wherein the correction lens possesses a short focal length $f$ shorter than 50 mm, and preferably shorter than 30 mm.

4. A method according to claim 1, wherein a reticle positioned in the Fabry-Perot cavity and centered on the main optical axis is used, and wherein the eye is aligned laterally relative to the main optical axis in such a manner that the reticle as seen by the eye is not deformed.

5. A method according to claim 4, wherein a converging correction lens is interposed between the eye and the reflecting element, the lens being centered on the main optical axis and serving to reduce sensitivity to lateral misalignment of the eye relative to the main optical axis, and wherein the reticle is positioned between the reflecting element and the correction lens in the focal plane of the correction lens.

6. A method according to claim 1, wherein a reticle positioned in the Fabry-Perot cavity and centered on the main optical axis is used, and wherein the eye is aligned longitudinally on the main optical axis in such a manner that this reticle is visible to the eye.

7. A method according to claim 6, wherein a converging correction lens is interposed between the eye and the reflecting element, the lens being centered on the main optical axis and serving to reduce sensitivity to lateral misalignment of the eye relative to the main optical axis, and wherein the reticle is positioned between the reflecting element and the correction lens in the focal plane of the correction lens.

8. A method according to claim 1, wherein a converging lens and two reticles disposed on either side of the second lens and centered on the optical axis of said lens are used, and wherein in order to monitor lateral alignment of the eye relative to the main optical axis, both reticles are illuminated by means of an incoherent light beam and the eye is aligned laterally relative to the main optical axis in such a manner that the images of the two reticles seen by the eye are superposed.

9. A method according to claim 1, wherein a converging lens and two reticles disposed on either side of the second lens and centered on the optical axis of said lens are used, and wherein the longitudinal alignment of the eye on the main optical axis is monitored by illuminating both reticles by means of an incoherent light beam, and the intensity of the return beam reflected by the eye is monitored.

10. A method according to claim 8, wherein the two reticles are identical and positioned at a distance 2f' from the second lens, where f' is the focal length of the second lens.

11. A method according to claim 8, wherein a converging correction lens is interposed between the eye and the reflecting element, the lens being centered on the main optical axis and serving to reduce sensitivity to lateral misalignment of the eye relative to the main optical axis, and wherein one of the two reticles is positioned at a distance 2f from the correction lens, where $\underline{f}$ is the focal length of said lens.

12. A method according to claim 1, wherein once the eye has been aligned longitudinally and laterally relative to the main optical axis, the cornea is set into vibration by a blink of the eyelid or by a plurality of repeated blinks of the eyelid.

13. A method of measuring the intraocular pressure of an eye by setting it into vibration and detecting at least one mode of vibration of the eye in accordance with the method specified in claim 1.

14. A detection device for using laser interferometry to detect at least one natural mode of vibration of an eye, wherein the device comprises a Fabry-Perot cavity having a main optical axis and two reflecting faces, one of the two reflecting faces being formed by a reflecting element aligned on the optical axis, and the other reflecting face being formed, when the device is in use, by the cornea of the eye in which it is desired to detect at least one natural mode of vibration, a laser source for emitting an incident laser beam centered on the main optical axis of the cavity, and an optoelectronic detector for detecting the intensity I of longitudinal interference between the go and the return beams reflected along the main optical axis between the two reflecting faces of the Fabry-Perot cavity.

15. A detection device according to claim 14, including a converging correction lens positioned between the two reflecting faces of the Fabry-Perot cavity, the lens being centered on the main optical axis and serving to reduce sensitivity to lateral misalignment of the eye.

16. A device according to claim 15, wherein the correction lens possesses a short focal length $\underline{f}$ of less than 50 mm, and preferably of less than 30 mm.

17. A device according to claim 14, wherein in order to monitor the longitudinal alignment of the eye along the main optical axis and/or the lateral alignment of the eye relative to the main optical axis, use is made of a reticle positioned on the main optical axis between the two reflecting faces of the Fabry-Perot cavity.

18. A device according to claim 17, including a converging correction lens positioned between the two reflecting faces of the Fabry-Perot cavity, the lens being centered on the main optical axis and serving to reduce sensitivity to lateral misalignment of the eye, and wherein the reticle is positioned between the reflecting element and the correction lens in the focal plane of the correction lens.

19. A device according to claim 14, wherein in order to monitor the longitudinal alignment of the eye on the main optical axis and/or the lateral alignment of the eye relative to the main optical axis, the device includes a converging lens and two reticles disposed on either side of the second lens and centered on the optical axis of said lens, and a light source enabling the two reticles to be illuminated by means of an incoherent light beam.

20. A device according to claim 19, wherein the two reticles are identical and are positioned at a distance 2f' from the second lens, f' being the focal length of the second lens.

21. A device according to claim 19, including a converging correction lens positioned between the two reflecting faces of the Fabry-Perot cavity, the lens being centered on the main optical axis and serving to reduce sensitivity to lateral misalignment of the eye, and wherein one of the two reticles is positioned at a distance 2f from the correction lens, where $\underline{f}$ is the focal length of said lens.

* * * * *

UNITED STATES PATENT AND TRADEMARK OFFICE
CERTIFICATE OF CORRECTION

PATENT NO. : 7,441,898 B2  Page 1 of 1
APPLICATION NO. : 10/398673
DATED : October 28, 2008
INVENTOR(S) : Jaouad Zemmouri et al.

It is certified that error appears in the above-identified patent and that said Letters Patent is hereby corrected as shown below:

Column 1, line 30, "leads-to" should read --leads to--;

Column 6, line 5, "mounts-of-the-same" should read --mounts of the same--;

Column 6, line 7, "units 0" should read --units O--;

Column 7, line 40, (4), "$L(t) = L_0 + I^{-t/c}.\sin(wt)$" should read --$L(t) = L_0 + \ell^{-t/c}.\sin(wt)$--

Column 7, line 43, "l represents" should read --$\ell$ represents--; and

Column 9, line 55, "f or" should read --for--.

Signed and Sealed this

Fourth Day of August, 2009

JOHN DOLL
*Acting Director of the United States Patent and Trademark Office*